(12) United States Patent
Tsai et al.

(10) Patent No.: US 8,952,205 B2
(45) Date of Patent: Feb. 10, 2015

(54) METHOD FOR PRODUCING METHOXYPOLYETHYLENE GLYCOLS

(71) Applicant: Xiamen Ju Sheng Mechanical Engineering Co., Ltd., Xiamen (CN)

(72) Inventors: I-Min Tsai, Xiamen (CN); Kun Li, Xiamen (CN); Yanzhen Huang, Xiamen (CN); Xiaobin Wang, Xiamen (CN); Kechang Li, Xiamen (CN); Weiming Wu, Xiamen (CN)

(73) Assignee: Xiamen Ju Sheng Mechanical Engineering Co., Ltd., Xiamen (CN)

( * ) Notice: Subject to any disclaimer, the term of this patent is extended or adjusted under 35 U.S.C. 154(b) by 0 days.

(21) Appl. No.: 14/164,795

(22) Filed: Jan. 27, 2014

(65) Prior Publication Data

US 2014/0213829 A1     Jul. 31, 2014

(30) Foreign Application Priority Data

Jan. 28, 2013    (CN) .......................... 2013 1 0031964

(51) Int. Cl.
*C07C 41/03*    (2006.01)
(52) U.S. Cl.
CPC ...................................... *C07C 41/03* (2013.01)
USPC .......................................................... 568/679

(58) Field of Classification Search
None
See application file for complete search history.

(56) References Cited

PUBLICATIONS

Zhang et al., Journal of Applied Polymer Science (2007), 105(6), pp. 3780-3786.*

* cited by examiner

*Primary Examiner* — Brian J Davis
(74) *Attorney, Agent, or Firm* — Rabin & Berdo, P.C.

(57) ABSTRACT

A method for producing methoxypolyethylene glycols includes the steps of, in the order recited: (1) preparing a reactor by washing the reactor with water; pressurizing the reactor with nitrogen; and evacuating to completely remove water and reduce oxygen content in the reactor; (2) pressurizing the reactor with nitrogen, introducing ingredients including methanol and a catalyst comprised of sodium methoxide in methanol into the reactor, and heating the ingredients; (3) introducing ethylene oxide into the reactor at a rate of 800~1200 kg/h and reacting the methanol and the ethylene oxide to completely react the methanol; (4) introducing additional ethylene oxide into the reactor at a rate of 8000~12000 kg/h to continue the reaction and provide final reaction products; (5) reducing the pressure in the reactor and adjusting pH of the reaction products to a ph of 5 to 7; and (6) transferring the reaction products to a tank yard.

6 Claims, 1 Drawing Sheet

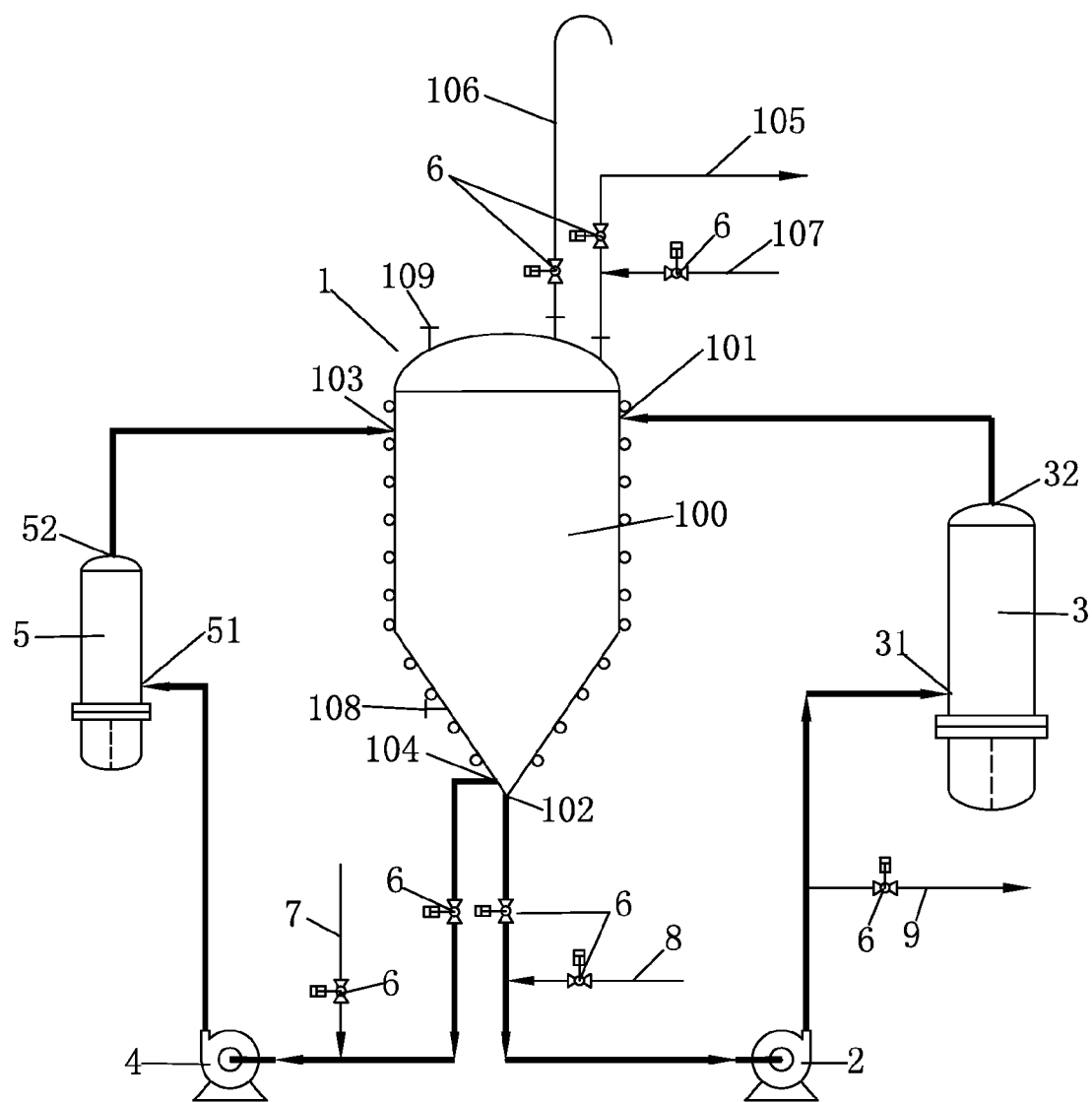

METHOD FOR PRODUCING METHOXYPOLYETHYLENE GLYCOLS

FIELD OF THE INVENTION

The present invention is relates to chemical products manufacturing field, more particularly to a method for producing methoxypolyethylene glycols.

BACKGROUND OF THE INVENTION

Methoxypolyethylene glycols with good water solubility, wettability, lubricity, physiological inertia, no irriation to human body and tenderness are widely used in cosmetics and pharmaceutical industry. The methoxypolyethylene glycols with different molecular scales are used for changing the viscosity, hygroscopicity and structure of product. The methoxypolyethylene glycols with low relative molecular weight (less than 2000) are fit for lubricant and consistency regulator in cream, emulsion, toothpaste, shaving cream, etc. The methoxypolyethylene glycols with high relative molecular weight are fit for lipstick, deodorant stick, toilet soap, shaving soap, foundation make-up, beauty products, etc. Methoxypolyethylene glycols can also be used for suspending agent and thickening agent in detergent. And in pharmaceutical industry, methoxypolyethylene glycols can be the matrix of ointment, emulsion, ointment, lotion and suppository.

Methoxypolyethylene glycols are obtained from the reaction between methanol and ethylene oxide, and the by-product PEG can be generated from the reaction between ethylene oxide and water in the reactor during the producing process, so a lot of absolute methanol or absolute ethanol is used for washing the reactor and removing water inside to avoid the production of the by-product and to reduce the consumption of ethylene oxide during the producing process of methoxypolyethylene glycols at the prior art with high production cost. Furthermore, the adding rate of ethylene oxide is low and causes long reaction time at the prior art, so that the synthetic process of methoxypolyethylene glycols is relative long.

SUMMARY OF THE INVENTION

The object of the present invention is to offer a method for producing methoxypolyethylene glycols which overcomes the defects at the prior art.

The technical proposal solving the technical matter in the present invention is:

Method for producing methoxypolyethylene glycols, comprises the following steps:

(1) after the reactor is washed by water, nitrogen is filled in the reactor to elevate the pressure and then the reactor is vacuumized to completely remove water and reduce the oxygen content in the reactor;

(2) nitrogen is filled in the rector and pressure is elevated, and then methanol and sodium methoxide as the catalyst in methanol is added into the reactor, and then warming up;

(3) ethylene oxide is added into the reactor at 800~1200 kg/h to process the pre-reaction;

(4) ethylene oxide is added into the reactor at 8000~12000 kg/h to process the reaction after methanol and ethylene oxide in the reactor are completely reacted;

(5) the pressure of reaction product is reduced and pH of reaction product is adjusted to 5~7 after the reaction is finished, and then the reaction product is transferred to the tank yard.

In a preferred embodiment, the step (1) is: after the reactor is washed by water, nitrogen is filled in the reactor to elevate the pressure and then the reactor is vacuumized to $-0.954~-0.950$ $kg/cm^2 \cdot g$ to completely remove water and reduce the oxygen content in the reactor.

In a preferred embodiment, the step (2) is: nitrogen is filled in the rector and pressure is elevated to $-0.75$ $kg/cm^2 \cdot g$, and then methanol is added into the reactor below 80° C., and the 30 wt % sodium methoxide as the catalyst in methanol is added into the reactor, and then warming up to 90~100° C., so that the content of sodium methoxide is less than 140 ppm in total reaction products.

In a preferred embodiment, the step (3) is: ethylene oxide is added into the reactor at 800~1200 kg/h to process the pre-reaction of which the reaction temperature is 110~120° C. and the reaction pressure is less than 6 $kg/cm^2 \cdot g$.

In a preferred embodiment, the step (4) is: ethylene oxide is added into the reactor at 8000~12000 kg/h to process the reaction of which the reaction temperature is 165~180° C. and the reaction pressure is less than 5 $kg/cm^2 \cdot g$ after methanol and ethylene oxide in the reactor are completely reacted.

In a preferred embodiment, the step (5) is: the pressure of reaction product is reduced, and the temperature and pH of reaction product are chilled to 110° C. and adjusted to 5~7 after the reaction is finished, and then the reaction product is transferred to the tank yard after chilled to 80° C.

Compared with the technical proposal at the prior, the benefits of the present invention are:

1 nitrogen is filled in the reactor before adding methanol to remove water inside, so that the reaction between ethylene oxide and water to generate the by-product PEG is avoid, and the vacuum process can also remove the remaining oxygen in the reactor to enhance the purity of product;

2 nitrogen is filled in the reactor to elevate the pressure and then methanol is added, so that over gasification and too high partial pressure are prevented after methanol is added;

3 the dosage of the catalyst is controlled in the present invention to ensure that the sodium content in the product fulfills the demands;

4 ethylene oxide is added at a relative low rate at the beginning of the reaction to prevent the gasification of methanol and too high pressure in the reactor, so that the reaction can be processed safely; the adding rate of ethylene oxide is enhanced after methanol is completely reacted to enhance the reaction rate, cut down the synthesis reaction time and increase the output of the device;

5 temperature during the reaction process is controlled sectionally to enhance the security of the whole device.

BRIEF DESCRIPTION OF THE DRAWINGS

FIG. 1 shows the structure schematic view of the reactor in the method of the present invention.

DESCRIPTION OF THE PREFERRED EMBODIMENTS

With the following description of the drawings and specific embodiments, the invention shall be further described in details.

In FIG. 1, the reaction device used in the method for producing methoxypolyethylene glycols in the present invention comprises:

A reactor 1;

A main circulation heat exchanger 3, comprising a first feed inlet 31 and a first feed outlet 32;

A main circulation pump 2;

An assistant circulation heat exchanger 5, comprises a second feed inlet 51 and a second feed outlet 52;

And an assistant circulation pump 4 with lower starting quantity than the said main circulation pump 2;

The reactor 1 comprises a main body 100, a main circulation feed inlet 101, a main circulation feed outlet 102, an assistant circulation feed inlet 103, an assistant circulation feed outlet 104, a vacuumizing pipe 105, a evacuation pipe 106, a nitrogen input pipe, a methanol feed inlet 108 and a ethylene oxide feed inlet 109; the main circulation feed outlet 102 and the assistant circulation feed outlet 104 are both arranged at the bottom of the main body 100 of the reactor 1; automatic valves 6 are arranged on the vacuumizing pipe 105, the evacuation pipe 106, the nitrogen input pipe 107, the main circulation feed outlet 102 and the assistant circulation feed outlet 104 respectively;

The main circulation feed outlet 102 is communicated with the first feed inlet 31 of the main circulation heat exchanger 3 through the main circulation pump 2, and the first feed outlet 32 of the main circulation heat exchanger 3 is communicated with the main circulation feed inlet 101 of the reactor 1; the assistant circulation feed outlet 104 of the reactor 1 is communicated with the second feed inlet 51 of the assistant circulation heat exchanger 5 through the assistant circulation pump 4, and the second feed outlet 52 of the assistant circulation heat exchanger 5 is communicated with the assistant circulation feed inlet 103 of the reactor 1.

A catalyst inlet pipe 7 is arranged at the pipe between the assistant circulation feed outlet 104 of the reactor 1 and the assistant circulation pump 4, a neutralizer inlet pipe 8 is arranged at the pipe between the main circulation feed outlet 102 of the reactor 1 and the main circulation pump 2, a product outlet pipe 9 is arranged at the pipe between the main circulation pump 2 and the first feed inlet 31 of the main circulation heat exchanger, automatic valves 6 are arranged on the catalyst inlet pipe 7, the neutralizer inlet pipe 8 and the product outlet pipe 9 respectively.

The working process of the present reaction device in the method in the present invention is as follow: the material flow direction is shown by the arrow in FIG. 1, (1) Methanol is added into the reactor through the chain initial dose feed inlet 108 to reach the starting quantity of the assistant circulation pump 4, and then the assistant circulation pump 4 and the stirring device are started, 30% wt sodium methoxide in methanol is added into the reactor through the catalyst inlet pipe 7 to produce the initial product, and then ethylene oxide is added into the reactor at 800~1200 kg/h through the ethylene oxide feed inlet 109 to produce the middle product, and then the main circulation pump 2 is started when the amount of the middle product gets to the starting quantity of the main circulation pump 2;

(2) The adding rate of ethylene oxide is enhanced to 8000~12000 kg/h and is kept until the reaction is over to get the final product;

(3) During the working process of the main circulation pump 2 and the assistant circulation pump 4, the final product can be transferred to the tank yard through the product outlet pipe 9 after the sample is detected qualified.

Embodiment 1

Producing MPEG 400

(1) After the reactor is washed by water, nitrogen is filled in the reactor to elevate the pressure to 2 kg/cm² g and then evacuated to 1.1 kg/cm² g, and then the reactor is vacuumized to −0.952 kg/cm²·g, the process above is executed for 1~3 times to completely remove water and reduce the oxygen content in the reactor;

(2) Nitrogen is filled in the rector and pressure is elevated to −0.75 kg/cm²·g, and then 1260 kg methanol is added into the reactor below 80° C., and the 5 kg 30 wt % sodium methoxide as the catalyst in methanol is added into the reactor, and then warming up to 90~100° C.;

(3) 1964 kg Ethylene oxide is added into the reactor at 800 kg/h to process the pre-reaction of which the reaction temperature is 110~120° C. and the reaction pressure is less than 6 kg/cm²·g;

(4) 11776 kg Ethylene oxide is added into the reactor at 8000 kg/h to process the reaction of which the reaction temperature is 165~180° C. and the reaction pressure is less than 5 kg/cm²·g after methanol and ethylene oxide in the reactor are completely reacted;

(5) The circulation loop of the reactor is kept circulating for 20~30 min after ethylene oxide is added until the pressure in the reactor is below 1 kg/cm² g;

(6) The temperature and pH of reaction product are chilled to 110° C. and adjusted to 5~7 by acetic acid, and then the reaction product is transferred to the tank yard after chilled to 80° C.

After tested, the content of PEG is less than 0.5 wt % and the content of sodium methoxide is less than 140 ppm in the produced MPEG400.

Embodiment 2

Producing MPEG 1000

(1) After the reactor is washed by water, nitrogen is filled in the reactor to elevate the pressure to 2 kg/cm² g and then evacuated to 1.1 kg/cm² g, and then the reactor is vacuumized to ~0.952 kg/cm²·g, the process above is executed for 1~3 times to completely remove water and reduce the oxygen content in the reactor;

(2) Nitrogen is filled in the rector and pressure is elevated to −0.75 kg/cm²·g, and then 539 kg methanol is added into the reactor below 80° C., and the 5 kg 30 wt % sodium methoxide as the catalyst in methanol is added into the reactor, and then warming up to 90~100° C.;

(3) 774 kg Ethylene oxide is added into the reactor at 1000 kg/h to process the pre-reaction of which the reaction temperature is 110~120° C. and the reaction pressure is less than 6 kg/cm²·g;

(4) 13687 kg Ethylene oxide is added into the reactor at 10000 kg/h to process the reaction of which the reaction temperature is 165~180° C. and the reaction pressure is less than 5 kg/cm²·g after methanol and ethylene oxide in the reactor are completely reacted;

(5) The circulation loop of the reactor is kept circulating for 20~30 min after ethylene oxide is added until the pressure in the reactor is below 1 kg/cm² g;

(6) The temperature and pH of reaction product are chilled to 110° C. and adjusted to 5~7 by acetic acid, and then the reaction product is transferred to the tank yard after chilled to 80° C.

After tested, the content of PEG is less than 0.5 wt % and the content of sodium methoxide is less than 140 ppm in the produced MPEG1000.

Embodiment 3

Producing MPEG 2000

There are two main steps in this producing process:
First of all, MPEG350 is produced from methanol:

(1) After the reactor is washed by water, nitrogen is filled in the reactor to elevate the pressure to 2 kg/cm² g and then evacuated to 1.1 kg/cm² g, and then the reactor is vacuumized to −0.952 kg/cm²·g, the process above is executed for 1~3 times to completely remove water and reduce the oxygen content in the reactor;

(2) Nitrogen is filled in the rector and pressure is elevated to −0.75 kg/cm²·g, and then 1432 kg methanol is added into the reactor below 80° C., and the 50 kg 30 wt % sodium methoxide as the catalyst in methanol is added into the reactor, and then warming up to 90~100° C.;

(3) 2248 kg Ethylene oxide is added into the reactor at 1200 kg/h to process the pre-reaction of which the reaction temperature is 110~120° C. and the reaction pressure is less than 6 kg/cm²·g;

(4) 11320 kg Ethylene oxide is added into the reactor at 12000 kg/h to process the reaction of which the reaction temperature is 165~180° C. and the reaction pressure is less than 5 kg/cm²·g after methanol and ethylene oxide in the reactor are completely reacted;

(5) The circulation loop of the reactor is kept circulating for 20~30 min after ethylene oxide is added until the pressure in the reactor is below 1 kg/cm² g;

(6) The temperature and pH of reaction product are chilled to 110° C. and adjusted to 5~7 by acetic acid, and then the reaction product is transferred out of the reactor after chilled to 80° C.

Second, MPEG2000 is Produced from MPEG350:

(1) 2625 kg MPEG350 from the steps above and 4.1 kg 30 wt % sodium methoxide as the catalyst in methanol are added into the reactor of which the initial pressure is −0.5 kg/cm² g, and then warming up to 150° C.;

(2) Ethylene oxide (500 kg at most) is added into the reactor to elevate the pressure inside to 2 kg/cm² g, and then the pre-reaction between ethylene oxide and MPEG350 is processed, and then the next step is started after the pressure in the reactor is less than 1.5 kg/cm² g;

(3) 12375 kg Ethylene oxide is added into the main reactor to process the reaction with circulating catalyzed MPEG350, and the reaction temperature and the reaction pressure in the main reactor are kept at 165~180° C. and 2~5 kg/cm²·g through the external recirculation cooler;

(4) The temperature and pH of reaction product are chilled to 110° C. and adjusted to 5~7 by acetic acid, and then the reaction product is transferred out of the reactor after chilled to 80° C.

After tested, the content of PEG is less than 0.5 wt % and the content of sodium methoxide is less than 140 ppm in the produced MPEG2000.

The invention has been described with reference to the preferred embodiments mentioned above; therefore it cannot limit the reference implementation of the invention. It is obvious to a person skilled in the art that structural modification and changes can be carried out without leaving the scope of the claims hereinafter and the description above.

What is claimed is:

1. A method for producing methoxypolyethylene glycols, comprising, the steps of, in the order recited:
   (1) preparing a reactor by washing the reactor with water, pressurizing the reactor with nitrogen, and evacuating to completely remove water and reduce oxygen content in the reactor;
   (2) pressurizing the reactor with nitrogen, introducing reagents methanol and a catalyst comprised of sodium methoxide in methanol into the reactor, and heating the reagents;
   (3) introducing ethylene oxide into the reactor at a rate of 800~1200 kg/h and reacting the methanol and the ethylene oxide to completely react the methanol and provide initial reaction products;
   (4) introducing additional ethylene oxide into the reactor at a rate of 8000~12000 kg/h to continue the reaction, after the methanol is completely reacted in step (3), to provide final reaction products;
   (5) reducing the pressure in the reactor and adjusting pH of the final reaction products to a pH of 5 to 7 after the reaction is finished; and
   (6) transferring the final reaction products to a tank yard.

2. The method for producing methoxypolyethylene glycols according to claim 1, wherein evacuating to completely remove water and reduce oxygen content in the reactor is implemented to provide a pressure ranging from −0.954 to −0.950 kg/cm² (gauge).

3. The method for producing methoxypolyethylene glycols according to claim 2, wherein pressurizing the reactor with nitrogen provides a pressure of −0.75 kg/cm² (gauge) the methanol is introduced into the reactor at a temperature below 80° C., the catalyst comprises 30 wt % of sodium methoxide, and the reagents are heated to a temperature ranging from 90 to 100° C., and wherein sodium methoxide is present in the reaction products in an amount of less than 140 ppm.

4. The method for producing methoxypolyethylene glycols according to claim 3, wherein reacting the ethylene oxide and the methanol takes place at a reaction temperature ranging from 110 to 120° C. and at a reaction pressure of less than 6 kg/cm² (gauge).

5. The method for producing methoxypolyethylene glycols according to claim 4, wherein introducing additional ethylene oxide to continue the reaction includes adjusting temperature and pressure in the reactor to provide a reaction temperature ranging from 165 to 180° C. and a reaction-pressure that is less than 5 kg/cm² (gauge).

6. The method for producing methoxypolyethylene glycols according to claim 5, wherein adjusting the pH of the reaction products is preceded by reducing the temperature of the reaction products to 110° C., and wherein transferring the reaction products to the tank yard is preceded by adjusting the temperature of the reaction products to 80° C.

* * * * *